US00PP30351P3

(12) United States Plant Patent
Lynch

(10) Patent No.: US PP30,351 P3
(45) Date of Patent: Apr. 9, 2019

(54) APPLE TREE NAMED 'HARLEY05'

(50) Latin Name: *Malus domestica*
Varietal Denomination: Harley05

(71) Applicant: Fashion Foods Limited, Nelson (NZ)

(72) Inventor: William John Edmund Lynch, Richmond (NZ)

(73) Assignee: Fashion Foods Limited, Nelson (NZ)

( * ) Notice: Subject to any disclaimer, the term of this patent is extended or adjusted under 35 U.S.C. 154(b) by 0 days.

(21) Appl. No.: 14/999,875

(22) Filed: Jul. 13, 2016

(65) Prior Publication Data

US 2017/0020043 P1 Jan. 19, 2017

(30) Foreign Application Priority Data

Jul. 15, 2015 (NZ) ..... PBR APP233

(51) Int. Cl.
*A01H 5/08* (2018.01)

(52) U.S. Cl.
USPC ..... Plt./162
CPC ..... *A01H 5/08* (2013.01)

(58) Field of Classification Search
USPC ..... Plt./161, 162
CPC ..... A01H 5/0875
See application file for complete search history.

*Primary Examiner* — Kent L Bell
(74) *Attorney, Agent, or Firm* — Leydig, Voit & Mayer, Ltd.

(57) ABSTRACT

A new and distinct variety of *Malus domestica* named 'Harley05' characterized by a bright rose pink colour; foreground colour over 75% of fruit surface; mild cheddar background colour; prominent lenticel spots over surface area; early maturation; distinctive strong flavours and after-tastes; consistent and stable repeat cropping returning identical characteristics over an extended trial period; and retention and enhancement of bright colouration in long storage events.

7 Drawing Sheets

Genus and species plant claimed: *Malus domestica.*
Variety denomination: 'Harley05'.

CROSS REFERENCE TO RELATED APPLICATION

This application claims the benefit of New Zealand Plant Variety Rights Application No. APP233, filed Jul. 15, 2015, the disclosure of which is incorporated by reference in its entirety.

BACKGROUND OF THE INVENTION

The present invention relates to a new and distinct variety of apple tree hereinafter referred to as 'Harley05'.

The discovery was made in 1999 amongst a block of 'Heritage Gala' apple trees growing in a cultivated orchard in the Tasman District of Nelson Province in New Zealand, whereby one tree on the end of a row of trees was identified that exhibited many and varied apparent mutations of the variety that was systematically planted in an orchard block of apple trees. The parent tree is believed to be a 'Heritage Gala' tree, where 'Heritage Gala' refers to a historical New Zealand bred apple variety. Due to the location of the tree and its significant different attributes from all others, it was not possible to establish whether the tree was a seedling positioned strategically for expedient observation, or a chance mutation coincidentally occurring on the end of a row of trees, as the orchard was purchased with the trees established and enquiries failed to reveal any knowledge or information.

The inventor selected and propagated trees from the identified discovery to test and consider the attributes of the discovery, and after many years of observation, trials and elimination chose two principal new apple varieties that were distinctly different visually and in plant performance, and eating attributes.

'Harley05' is one of the chosen selections and was propagated from the selected plant material and planted out on rootstocks M.793, M9, and CG202 in moderate numbers to further test and examine stability and identified characteristics. The parent tree grew on M793 rootstock spaced 5 m×3 m and grew vigorously. The instant variety is propagated on Malling 9 rootstock with spacing of 1.5 m×3.5 m with lesser vegetative vigor.

BRIEF DESCRIPTION OF THE INVENTION

Over a 15 year trial period the inventor has established the following characteristics and differences that demonstrate 'Harley05' as a new and distinct apple variety: 1) Bright rose pink with very faint underline stripe sometimes visible, fully filling in to block colour; 2) More intensively visually apparent bright rose pink tones than any comparable early maturing apple varieties; 3) Foreground colour over 75% of fruit surface; 4) Mild cheddar background colour; 5) Prominent lenticel spots over surface area; 6) Early maturation affording harvest 7 to 10 days in advance of regular 'Gala' and 'Royal Gala' varieties; 7) Distinctive strong flavours and after-tastes more intense than 'Royal Gala' and its mutations, and discerningly different with a hint of acidity compared to 'Heritage Gala'; 8) Consistent and stable repeat cropping returning identical characteristics over an extended trial period; and 9) Retention and enhancement of bright colouration in long storage events, compared to fading and browning observed in regular 'Royal Gala' and 'Gala' strains when stored for extended periods.

Provided below are comparisons of the present variety to possible parental or other early maturing varieties.

TABLE 1

| Characteristic | New Variety 'Harley05' | Comparison variety |
|---|---|---|
| Hue over colour of mature fruit | bright rose pink | 'Heritage Gala' orange/red 'Royal Gala' orange/red |
| Background colour at optimum harvest | mild cheddar | lemon |
| Relative area of over-colour | 75%-95% | 'Heritage Gala' 25%-50% 'Royal Gala' 50%-80% |
| Relative area of background colour | 5%-25% | 'Heritage Gala' 50%-75% 'Royal Gala' 25%-50% |
| Relative area of lenticel spots | 90%-100% | 'Heritage Gala' 0% |
| Relative eating attributes | stronger flavours and after-tastes | 'Royal Gala' noticeably lesser than traditional 'Gala' & 'Royal Gala' |

BRIEF DESCRIPTION OF THE DRAWINGS

The accompanying photographs illustrate the overall appearance of the new *Malus* variety 'Harley05' showing the colours as true as is reasonably possible with coloured reproductions of this type (using a 41 mp camera).

DETAILED DESCRIPTION

Figure 1:
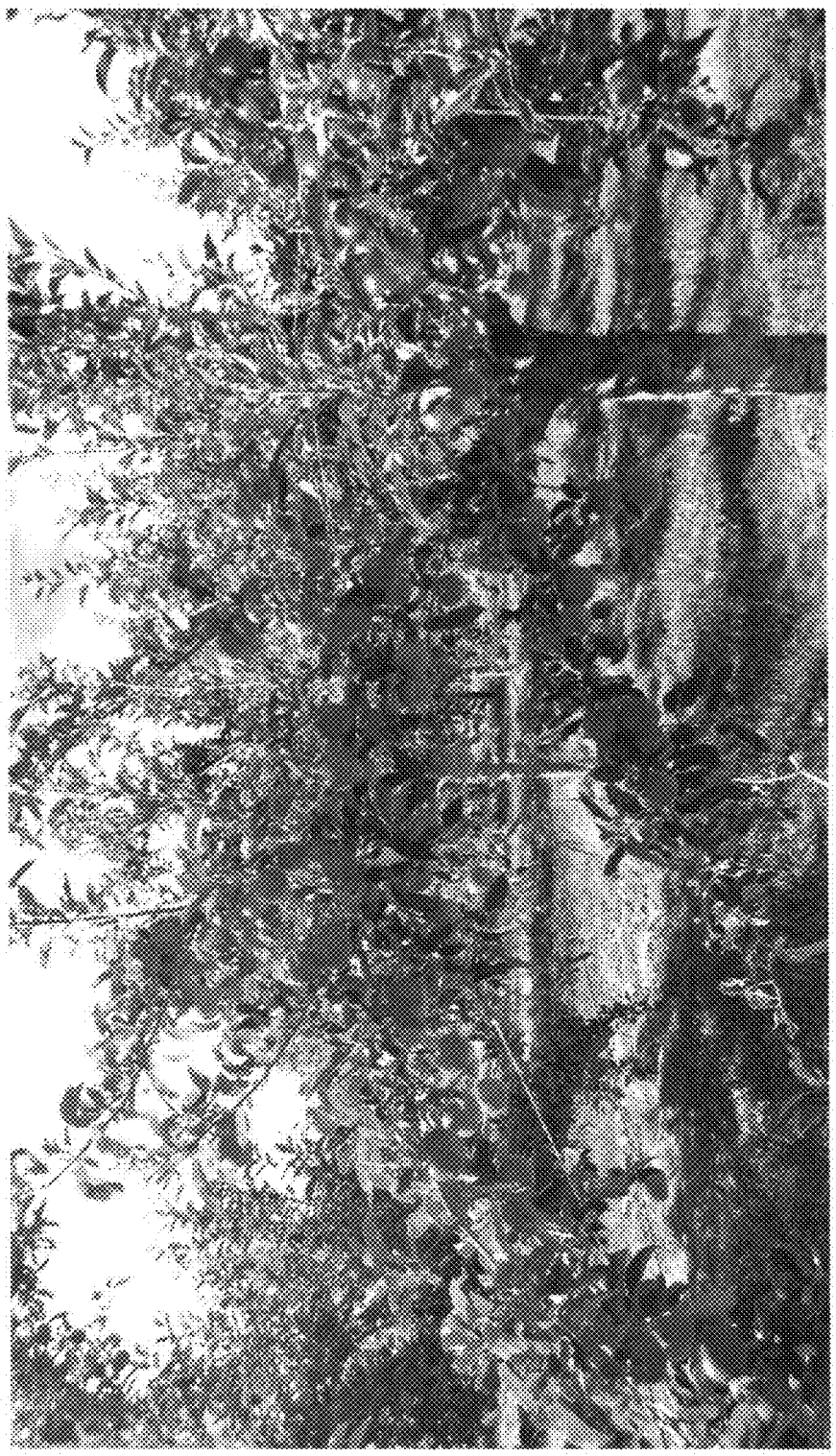
FIG. 1 shows a perspective view of cropping 'Harley05' trees with fruit immediately prior to harvest.
Figure 2:
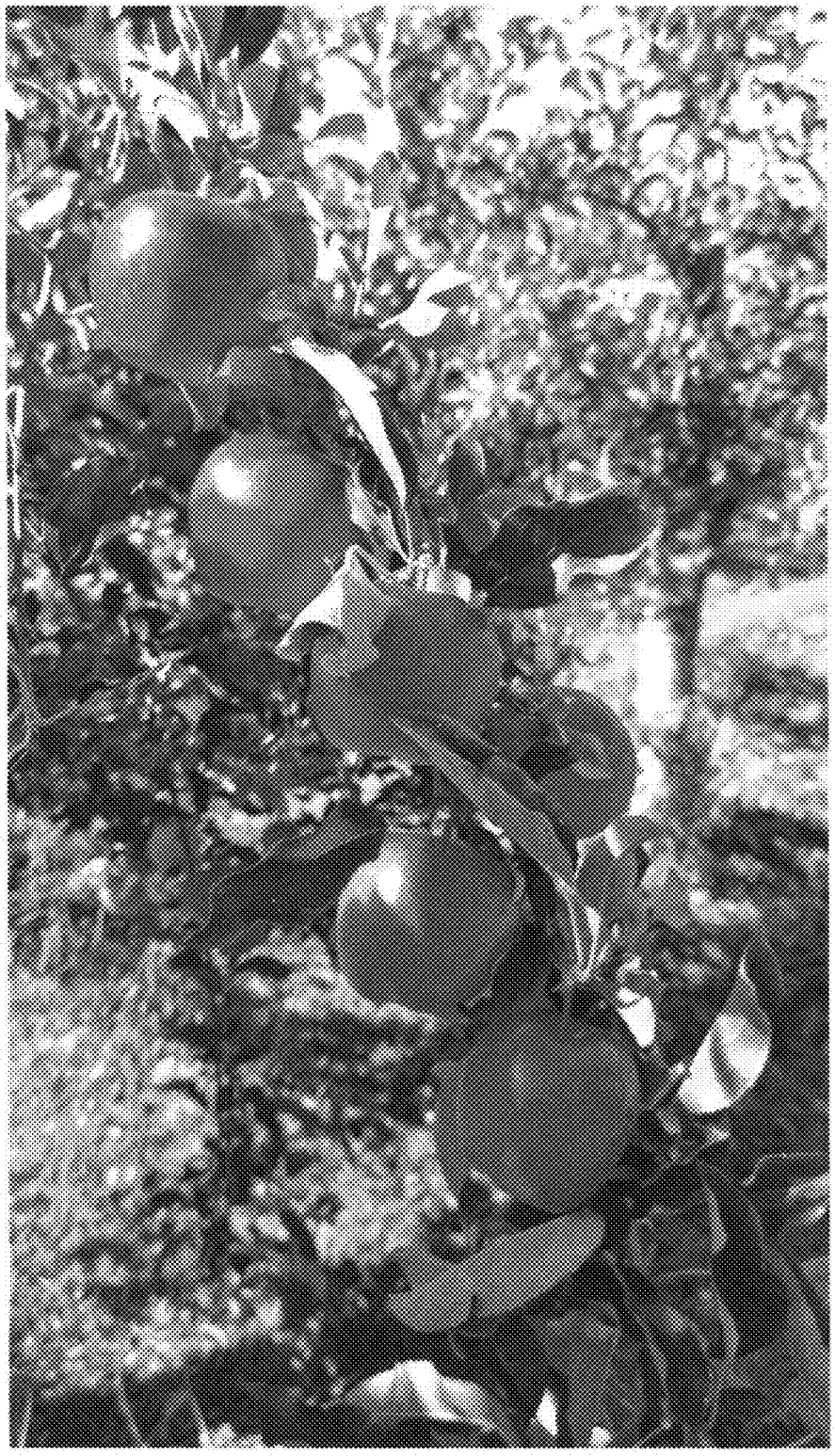
FIG. 2 shows a closer perspective view of cropping 'Harley05' trees with fruit immediately prior to harvest.
Figure 3:
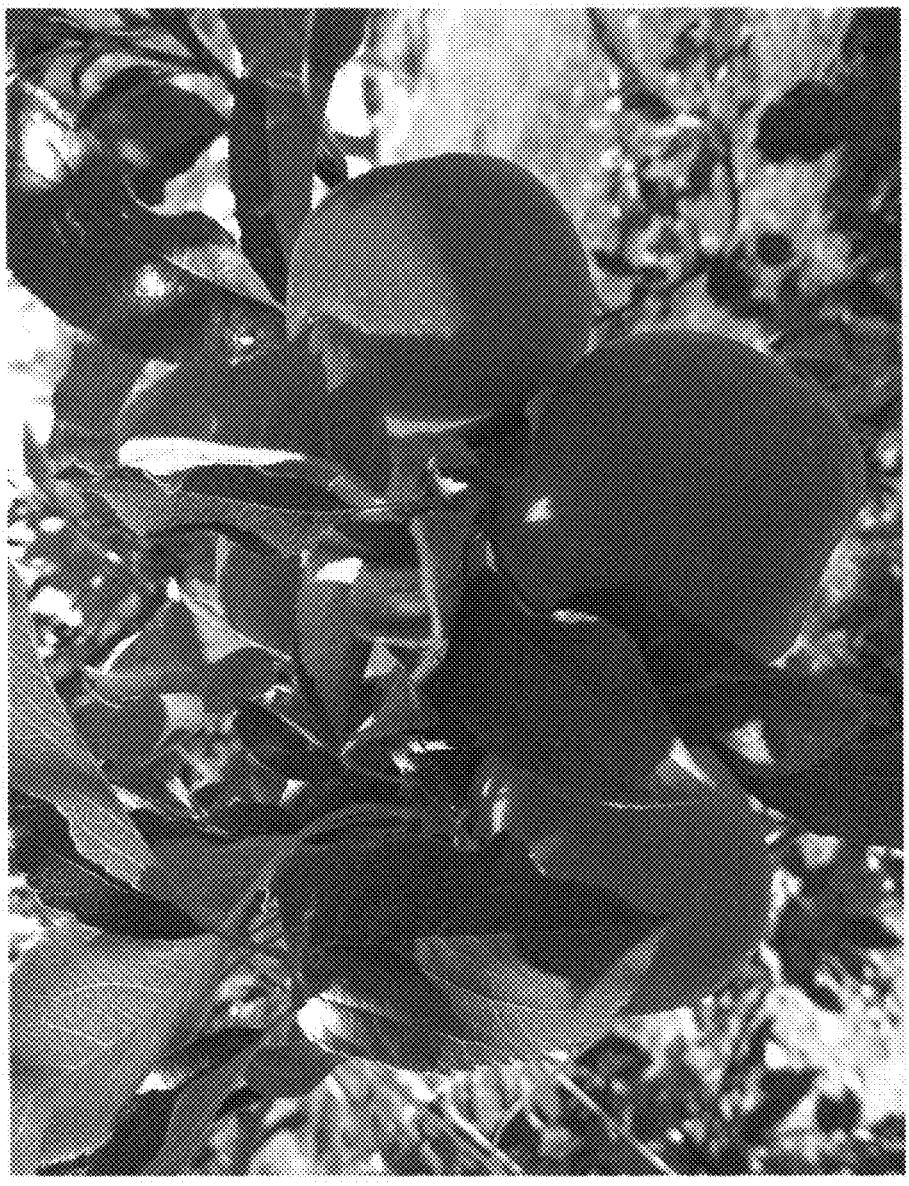
FIG. 3 shows a perspective view of 'Harley05' exhibiting forward maturation fruits 3 weeks prior to 'Royal Gala' harvest commencement.
Figure 4:
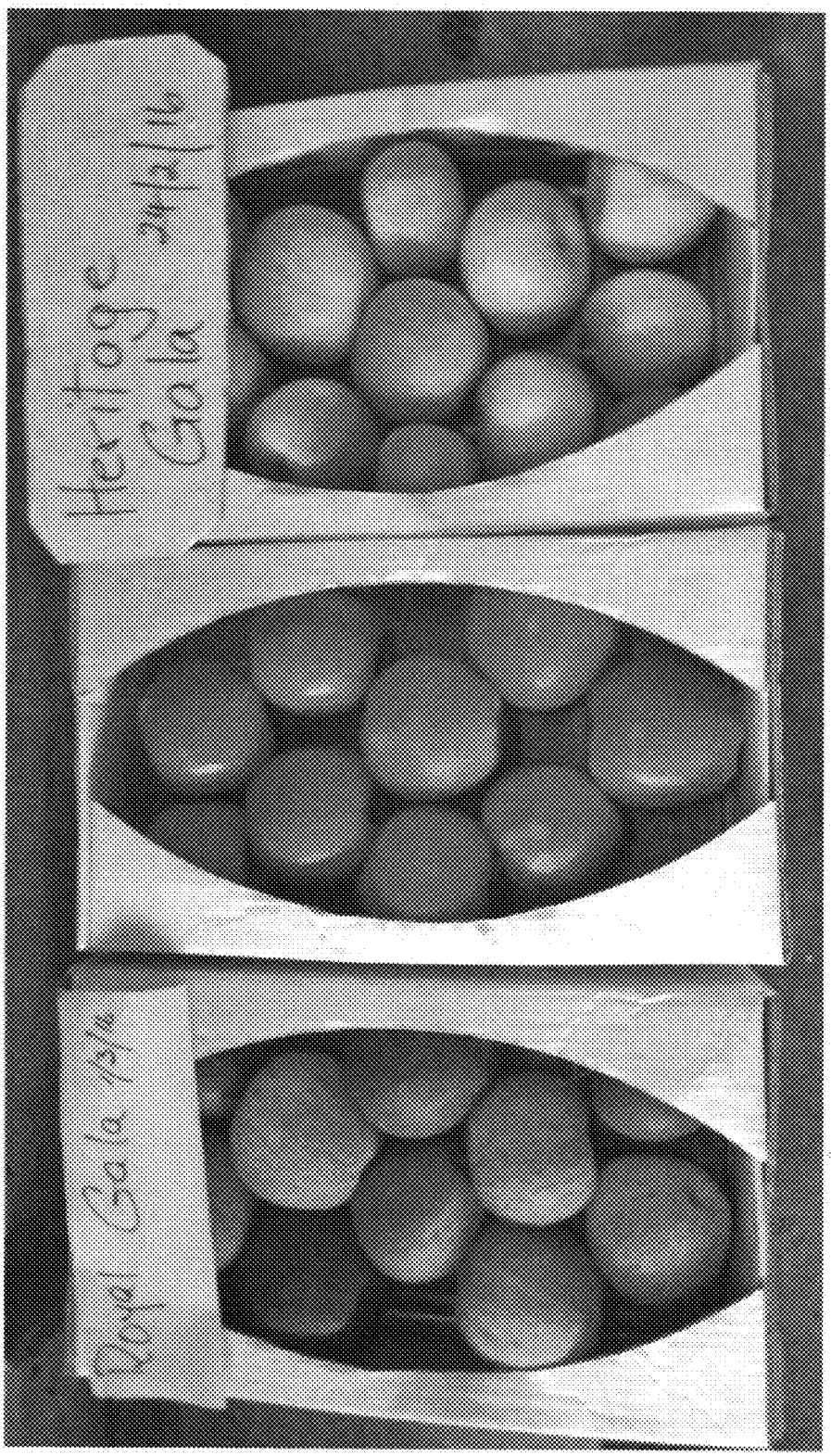
FIG. 4 shows a perspective comparison of harvested 'Harley05' fruit alongside 'Heritage Gala' and 'Royal Gala' exhibiting distinctive visual differences.
Figure 5:
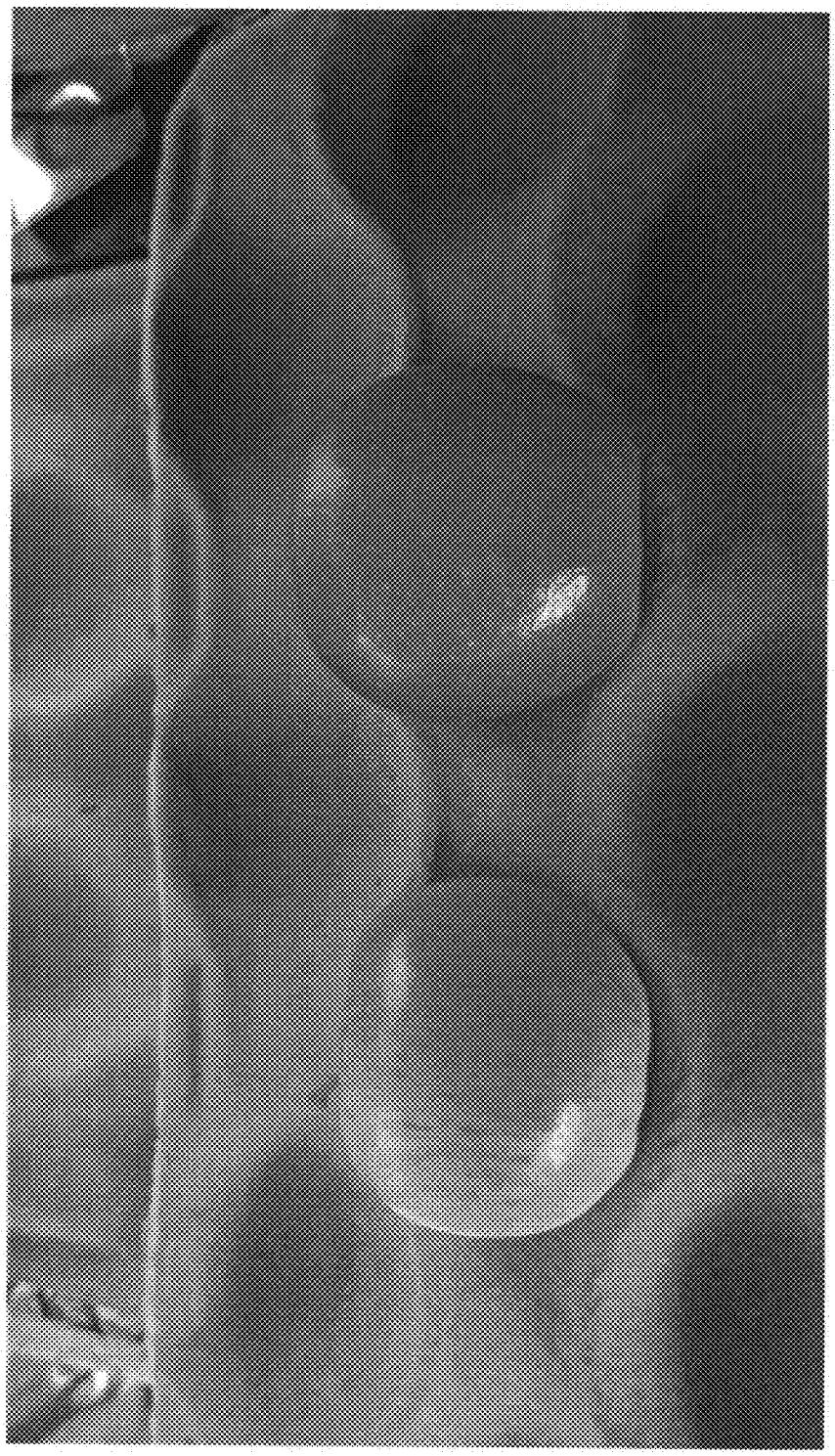
FIG. 5 shows 'Harley05' prominent lenticel spots.
Figure 6:
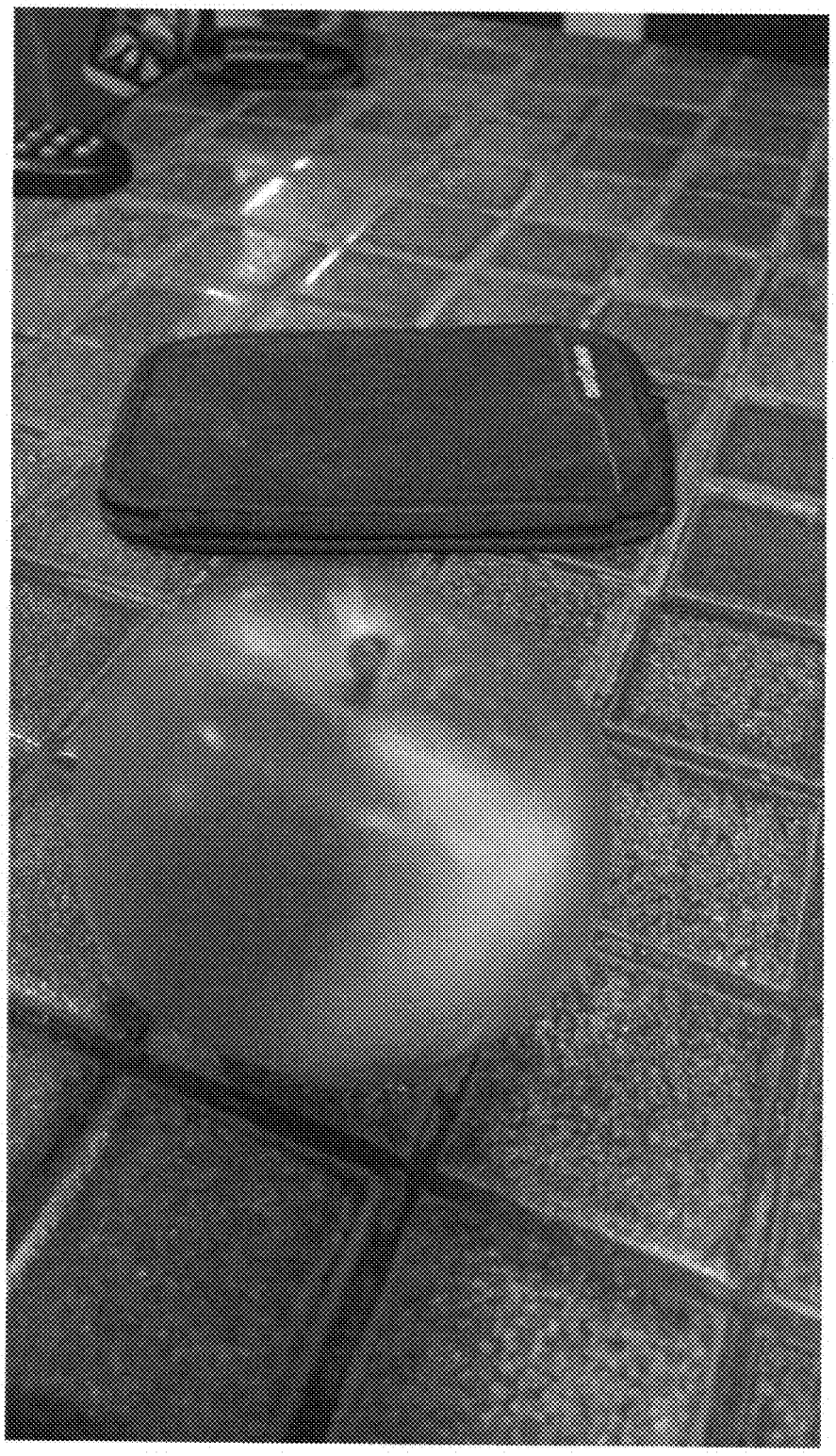
FIG. 6 shows mild cheddar background colour.
Figure 7:
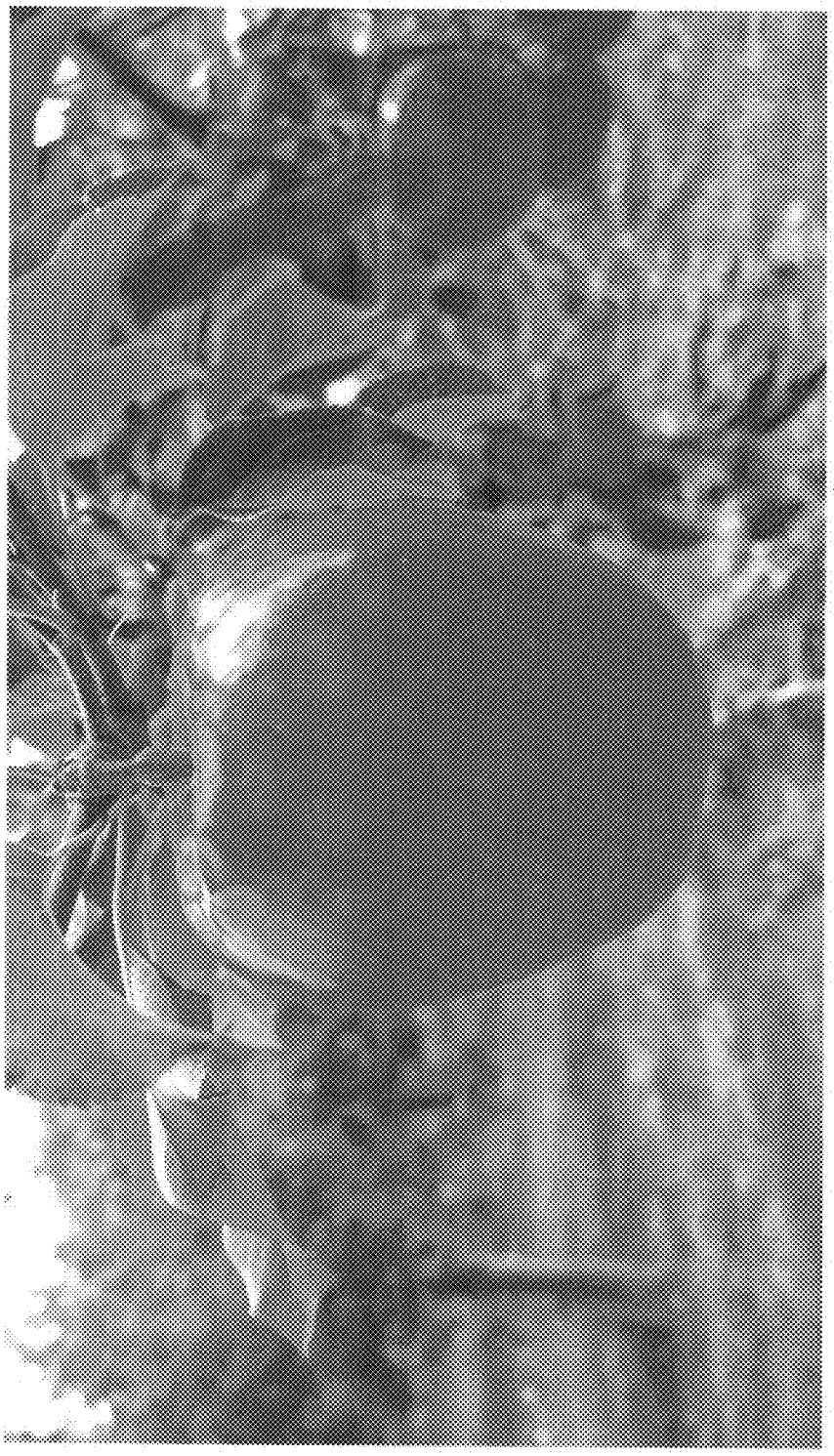
FIG. 7 shows vivid rose pink colouration capability.

The following is a detailed description of the new variety with colour terminology in accordance with The Royal Horticultural Society Colour Charts (R.H.S.C.C.).

The new *Malus* variety 'Harley05' has not been observed under all possible environmental conditions.

The aforementioned photographs together with the following observations and values, describe the trees of 'Harley05' as grown in the orchard in Redwood Valley, Tasman District, Nelson Province of the South Island of New Zealand, Latitude S. 41, E2516661, N5989297, 36-50 m above sea level.

The planting site and climatic conditions closely approximate those generally used in commercial production of pipfruit, and the land areas in the vicinity have successfully been deployed in the production of pipfruit since the settlement of the Region, so that the location is generally viewed as a suitable site for commercial production.

The climate is in the temperate zone with summer temperatures generally below 30 deg C. and maximum 35 deg C. Winter temperatures range 7-16 deg C. with minimums minus 5-7 deg C.

The soil is variable and of modest fertility, being a mix of recent alluvial soils with clay type sub-soil, with fertility maintained by applications of fertiliser applied annually.

Trees are irrigated by drip irrigation when necessary. Annual rainfall is 900-1200 mm per year.

The trial blocks are substantially planted on CG 202 rootstock with the first commercial planting trial block now in 6th year. Plantings are spaced 1.5 M between tree and 3.5 m row width giving a tree density of about 2000 trees per hectare. All trees have performed identically in respect of fruit characteristics.

The type of bearing is early, being the first harvestable variety on the orchard. Productivity is good with regular and heavy return flowering and no bi-annual flowering evident.

Production on mature trees is estimated to be 20 kg-30 kg per tree.

Average size of mature trees is 3 m height and spread 1.4 m.

Trunk calliper is around 5 cm (10 cm above grafting).

Trunk texture is smooth with numerous lenticels moderately raised. Trunk lenticel height=1 mm. Width=5 mm. Density=4.5 lenticels per sq cm. Colour=148D.

Trunk bark colour brown-greyed RHS 243.

Branches number about 15 per tree, typically 7 or 8 permanent braches, and are angled generally 45-75 deg. Average length=85 cm. Average diameter 2.5 cm. Internode length 2.5 cm. Colour=148B. Natural growth tendencies have been supressed by tying pendant as part of tree training management.

Leaf shape is elongated with heavily serrated margins. Typically 5 leaves to a cluster. Average length=10.00 cm. Average width 5.75 cm. Leaf base has unequal attachment to petioles. Leaves have an even venation pattern with approximately 6 ribs but erratic toward apex. Venation pattern is arcuate at about 45 deg towards the apex. The front surface texture is waxy and the rear surface texture is dry. Front surface colour is RHS141A. Reverse surface colour is RHS 137C.

Petiole length=4.5 cm, with a diameter of 2 cm. Petiole colour=138A.

Blooming time at the Redwood Valley trial site is from early October until the 3rd week of October with staggered later heavy flowering on one year old wood. The flowers are borne in clusters with approximately 6 flowers per cluster. Flowers can also be borne singly. The average flower depth is 16 mm and flower diameter is 40 mm.

The flower bud shape is bulbous, round with an average bud length of 14 mm and bud diameter of 9 mm. The flower bud colour is 134B. The average number of petals is 5, with an average petal length of 29 mm and petal width of 12 mm. The petals have an oval tapered—obovate shape. The petal apex is rounded with no distinct point (rotundifolus). The petal margin is entire (forma integra). The abaxial petal texture is soft, smooth and lightly veined, while the adaxial petal texture is soft and veined. The abaxial and adaxial surfaces of the petal both have a colour of 62D.

The average number of sepals is 5, with an average sepal length of 9 mm and sepal width of 4 mm. The sepals have a triangular shape to a pointed tip. The sepal apex is sharp and pointed. The sepal margin is fringed by hairs (ciliatus). The abaxial sepal texture and the adaxial sepal texture are both lightly furnished by hairs. The abaxial and adaxial surfaces of the sepal both have a colour of 134B.

Fruit maturity commences early February which is about 125 days after flowering.

The harvest window is from early-mid February until early March.

Keeping quality is good on the tree and in storage. In Coolstore at 0.5 deg C. trials with Smartfresh™ have stored good quality outcomes to 280 days. Shipping trials performed in 2017 indicate good storage and handling characteristics, with up to 200 days post-harvest on trials to date.

Fruits are conical-truncated with average fruit height of 70 mm, fruit diameter of 77 mm, and weight around 240 gm.

Stem length is around 45 mm with a diameter of 3 mm. Colour of the stem is 20A.

Stem cavity depth is 9 mm with a width of 34 mm and has small areas of smooth russet on about 30% of the fruits.

The typical observed eye basin width is 32 mm and eye basin depth is 16 mm. The crowning at the apex contains very slight crowns, and the sepals are positioned at the base of the petals. The calyx tube forms a cuplike funnel.

Skin is smooth texture of medium thickness.

Firmness at harvest time 7.6 kg-9.9 kg.

Colour is around RHS 55A with background around 4B. The fruit pattern overcolour is bright pink/red. Fruit flesh texture is crisp and juicy, with a sugar content of 12.4. The fruit flesh colour is 2C.

The fruit core is oblongated. Approximately 5 fruit locule per fruit, where the fruit locule form contains separate chambers that are seed shaped. The average fruit locule length is 16 mm and average fruit locule width is 4 mm. Seeds per fruit is about 6 and per locule generally 2. The seeds are teardrop shaped with a smooth texture and a colour of 177A. Seed length is 8.5 mm-width 5 mm.

The typical number of pistils is 5 and the average pistil length is 12 mm. The average anther length is 2.5 mm with a colour of 2C. The average stigma length is 0.5 mm with a colour ot 142C. The average style length is 8 mm with a colour of 142C. The average ovary length is 2.5 mm with a colour of 130A. The pollen amount is abundant and the pollen has a colour of 14A.

Propagation is from budding and grafting on GC202 (patented) rootstock.

Light intensities—full sunlight or slight shade. A small trial area using light-reflective cloth has been conducted with anticipated outcome of increased percentage of foreground colour and earlier harvest.

Pruning requirements are similar to heritage 'Gala', requiring removal of strong upright growth, and systematic renewal of fruiting wood. The trees perform well with branches trained into a pendant position of approximately 45% below horizontal. Flower numbers are very high and require heavy blossom thinning over the bloom period.

Tree vigour is moderate with upright form and good ramification.

Main branches develop with flat angles around 45%-50% if not trained down.

Use is the fresh fruit market as a desert apple from March until December in NZ.

Disease/pest susceptibility is evident to black spot (scab), and powdery mildew at increased incidence requiring dedicated control.

Climatic hardiness appears normal tolerance for planted site which experiences summer temperatures in the mid to high 30's (Celsius) and winter temperatures down to −10 deg C.

I claim:

1. A new and distinct apple tree named 'Harley05' as illustrated and described herein.

* * * * *